(12) United States Patent
Takaishi et al.

(10) Patent No.: US 8,796,176 B2
(45) Date of Patent: Aug. 5, 2014

(54) PESTICIDAL COMPOSITION COMPRISING AN ALPHA-ALKOXYPHENYL ACETIC ACID DERIVATIVE AND A NEONICOTINOID COMPOUND

(75) Inventors: Masanao Takaishi, Toyonaka (JP); Atsushi Iwata, Takarazuka (JP)

(73) Assignee: Sumitomo Chemical Company, Ltd, Tokyo (JP)

( * ) Notice: Subject to any disclaimer, the term of this patent is extended or adjusted under 35 U.S.C. 154(b) by 189 days.

(21) Appl. No.: 13/119,606

(22) PCT Filed: Sep. 17, 2009

(86) PCT No.: PCT/JP2009/066835
§ 371 (c)(1),
(2), (4) Date: Apr. 29, 2011

(87) PCT Pub. No.: WO2010/032871
PCT Pub. Date: Mar. 25, 2010

(65) Prior Publication Data
US 2012/0270732 A1   Oct. 25, 2012

(30) Foreign Application Priority Data

Sep. 19, 2008  (JP) .................................. 2008-241609
Nov. 25, 2008  (JP) .................................. 2008-299986

(51) Int. Cl.
| | | |
|---|---|---|
| A01N 37/18 | (2006.01) | |
| A01N 37/38 | (2006.01) | |
| A01N 43/08 | (2006.01) | |
| A01N 43/40 | (2006.01) | |
| A01N 43/50 | (2006.01) | |
| A01N 43/78 | (2006.01) | |
| A01N 43/88 | (2006.01) | |
| A01N 47/40 | (2006.01) | |
| A01N 51/00 | (2006.01) | |
| A01P 3/00 | (2006.01) | |
| A01P 7/04 | (2006.01) | |

(52) U.S. Cl.
USPC ........ 504/100; 514/229.2; 514/341; 514/342; 514/357; 514/365; 514/471; 514/617; 514/622

(58) Field of Classification Search
USPC .............. 514/365, 617, 622, 229.2, 341, 342, 514/357, 471; 504/100
See application file for complete search history.

(56) References Cited

U.S. PATENT DOCUMENTS

| | | | | |
|---|---|---|---|---|
| 5,034,404 A | * | 7/1991 | Uneme et al. ................. | 514/365 |
| 5,948,819 A | | 9/1999 | Ohtsuka et al. | |
| 6,436,968 B1 | | 8/2002 | Erdelen et al. | |
| 6,586,365 B2 | * | 7/2003 | Asrar et al. ................... | 504/100 |
| 6,689,356 B1 | | 2/2004 | Zlotkin et al. | |
| 8,188,122 B2 | | 5/2012 | Mihara et al. | |
| 2008/0234331 A1 | | 9/2008 | Fellmann et al. | |
| 2009/0143447 A1 | * | 6/2009 | Arthur et al. .................. | 514/370 |
| 2010/0120879 A1 | * | 5/2010 | Burgers et al. ................ | 514/383 |

FOREIGN PATENT DOCUMENTS

| | | |
|---|---|---|
| CA | 2686471 A1 | 12/1999 |
| CO | 6280438 A2 | 5/2011 |
| DE | 19829113 A1 | 12/1999 |
| DE | 03/000906 A | 1/2003 |
| EP | 0353191 A2 | 1/1990 |
| EP | 0374753 A2 | 6/1990 |
| EP | 0392225 A2 | 10/1990 |
| EP | 0427529 A1 | 5/1991 |
| EP | 0451878 A1 | 10/1991 |
| EP | 0754672 A1 | 1/1997 |
| JP | 2008-110971 A | 5/2008 |
| SU | 344616 A3 | 7/1992 |
| WO | 93/07278 A1 | 4/1993 |
| WO | 95/27693 A1 | 10/1995 |
| WO | 95/33818 A2 | 12/1995 |
| WO | 95/34656 A1 | 12/1995 |
| WO | 99/65313 A1 | 12/1999 |
| WO | WO 00/74484 * | 12/2000 |
| WO | 03/052073 A2 | 6/2003 |
| WO | 2006/023899 A1 | 3/2006 |
| WO | WO 2008/095924 * | 8/2008 |
| WO | WO 2008/095924 A2 | 8/2008 |

OTHER PUBLICATIONS

Nault, B.A. et al., "Performance of novel insecticide seed treatment for managing onion maggot (Diptera: Anthomyiidae) in onion fields," Crop Protection, vol. 25, pp. 58-65 (2006).*
Derwent Abstract 2001-102358, abstracting WO 00/74484 (Dec. 2000).*
Proceedings of the National Academy of Sciences USA, Sep. 1990, vol. 87, pp. 7175-7179.
Communication: International Search Report for International Patent Application No. PCT/JP2009/066835 mailed Feb. 5, 2010.
Japanese Office Action for corresponding Japanese Application No. 2008-299986 mailed May 23, 2013.
IN Office Action for corresponding IN Application No. W-00 2011 01009 mailed Sep. 6, 2013.
English translation of the Office Action for corresponding CO Application No. 11 031742 mailed Nov. 29, 2013.
Office Action for corresponding Russian Application No. 2011115234/13 (022603) issued Jun. 11, 2013.

* cited by examiner

Primary Examiner — John Pak

(57) ABSTRACT

PROBLEM
Provided is a composition for controlling pests having excellent control effect for pests and a method for controlling pests.
SOLUTION
A composition for controlling pests comprising an α-alkoxyphenylacetic acid compound and a neonicotinoid compound as active ingredients.

7 Claims, No Drawings

PESTICIDAL COMPOSITION COMPRISING AN ALPHA-ALKOXYPHENYL ACETIC ACID DERIVATIVE AND A NEONICOTINOID COMPOUND

This application is a national stage of PCT/JP2009/066835, filed on Sep. 17, 2009, which claims priority to the following applications: Japanese Patent Application No. 2008-241609, filed on Sep. 19, 2008; and Japanese Patent Application No. 2008-299986, filed Nov. 25, 2008. Each of these documents is incorporated herein by reference in its entirety.

TECHNICAL FIELD

The present invention relates to a composition for controlling pests and a method for controlling pests.

BACKGROUND ART

α-Substituted phenylacetic acid compounds are conventionally known as an active ingredient of a fungicide (for example, see PATENT DOCUMENT 1).
PATENT DOCUMENT 1: International Publication WO 95/27,693

DISCLOSURE OF THE INVENTION

Problems to be Solved by the Invention

An object of the present invention is to provide a composition for controlling pests having excellent control effect for pests and a method for controlling pests.

Means for Solving the Problems

The present invention provides a composition for controlling pests and a method for controlling pests in which control effect for pests has been improved by using an α-alkoxyphenylacetic acid compound represented by the following formula (1) among α-substituted phenylacetic acid compounds along with a neonicotinoid compound represented by the following formula (2).

That is, the present invention takes the following constitutions.

[1] A composition for controlling pests comprising, as active ingredients, an α-alkoxyphenylacetic acid compound represented by formula (1):

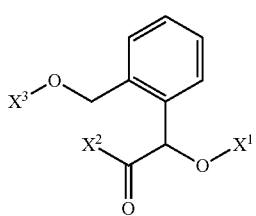

(1)

wherein $X^1$ represents a methyl group, a difluoromethyl group or an ethyl group; $X^2$ represents a methoxy group or a methylamino group; and $X^3$ represents a phenyl group, a 2-methylphenyl group or a 2,5-dimethylphenyl group;

and a neonicotinoid compound represented by formula (2)

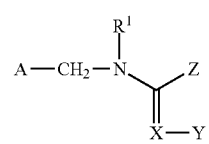

(2)

wherein A represents a 6-chloro-3-pyridyl group, a 2-chloro-5-thiazolyl group, a tetrahydrofuran-2-yl group or a tetrahydrofuran-3-yl group; Z represents a methyl group, an $NHR^2$ group, an $N(CH_3)R^2$ group or an $SR^2$ group; $R^1$ represents a hydrogen atom, a methyl group or an ethyl group; $R^2$ represents a hydrogen atom or a methyl group; or $R^1$ and $R^2$ together may form a $CH_2CH_2$ group or a $CH_2OCH_2$ group; X represents a nitrogen atom or a CH group; and Y represents a cyano group or a nitro group.

[2] The composition for controlling pests according to [1], wherein the neonicotinoid compound represented by formula (2) is selected from the group consisting of clothianidin, imidacloprid and thiamethoxam.

[3] The composition for controlling pests according to [1] or [2], wherein a weight ratio of the α-alkoxyphenylacetic acid compound represented by formula (1) to the neonicotinoid compound represented by formula (2) is in the range of 0.0125:1 to 500:1.

[4] A method for controlling pests which comprises applying effective amounts of the α-alkoxyphenylacetic acid compound represented by formula (1) of [1] and the neonicotinoid compound represented by formula (2) of [1] to the pests or a locus where the pests inhabit.

[5] A method for controlling pests which comprises applying effective amounts of the α-alkoxyphenylacetic acid compound represented by formula (1) of [1] and the neonicotinoid compound represented by formula (2) of [1] to a plant or a locus where a plant is allowed to grow.

[6] A seed treatment agent comprising the α-alkoxyphenylacetic acid compound represented by formula (1) of [1] and the neonicotinoid compound represented by formula (2) of [1] as active ingredients.

[7] A plant seed treated with effective amounts of the α-alkoxyphenylacetic acid compound represented by formula (1) of [1] and the neonicotinoid compound represented by formula (2) of [1].

[8] Combined use of the α-alkoxyphenylacetic acid compound represented by formula (1) of [1] and the neonicotinoid compound represented by formula (2) of [1] for controlling pests.

The composition for controlling pests according to the present invention exhibits an excellent effect against pests.

BEST MODE FOR CARRYING OUT THE INVENTION

The α-alkoxyphenylacetic acid compound represented by formula (1) for use in the composition for controlling pests according to the present invention is described.

Examples of the α-alkoxyphenylacetic acid compound represented by formula (1) includes the following compounds.

An α-alkoxyphenylacetic acid compound in which $X^1$ is a methyl group, a difluoromethyl group or an ethyl group in formula (1);

an α-alkoxyphenylacetic acid compound in which $X^1$ is a methyl group in formula (1);

an α-alkoxyphenylacetic acid compound in which $X^2$ is a methoxy group or a methylamino group in formula (1);

an α-alkoxyphenylacetic acid compound in which $X^1$ is a methyl group and $X^2$ is a methoxy group in formula (1);

an α-alkoxyphenylacetic acid compound in which $X^1$ is a methyl group and $X^2$ is methylamino group in formula (1);

an α-alkoxyphenylacetic acid compound in which $X^3$ is a phenyl group, a 2-methylphenyl group or a 2,5-dimethylphenyl group in formula (1);

an α-alkoxyphenylacetic acid compound in which $X^3$ is a phenyl group or a 2,5-dimethylphenyl group in formula (1);

an α-alkoxyphenylacetic acid compound in which $X^1$ is a methyl group, $X^2$ is a methoxy group, and $X^3$ is a 2,5-dimethylphenyl group in formula (1);

an α-alkoxyphenylacetic acid compound in which $X^1$ is a methyl group, $X^2$ is methylamino group, and $X^3$ is a phenyl group in formula (1); and an α-alkoxyphenylacetic acid compound in which $X^1$ is a methyl group, $X^2$ is methylamino group, and $X^3$ is a 2,5-dimethylphenyl group in formula (1).

Next, specific examples of the α-alkoxyphenylacetic acid compound represented by formula (1) are shown.

In the α-alkoxyphenylacetic acid compound represented by formula (1), $X^1$, $X^2$, $X^3$ are one of the combinations of substituents shown in Table 1.

TABLE 1

| $X^1$ | $X^2$ | $X^3$ |
|---|---|---|
| $CH_3$ | $OCH_3$ | Ph |
| $CH_3$ | $OCH_3$ | 2-$CH_3$Ph |
| $CH_3$ | $OCH_3$ | 2,5-$(CH_3)_2$Ph |
| $CH_3$ | $NHCH_3$ | Ph |
| $CH_3$ | $NHCH_3$ | 2-$CH_3$Ph |
| $CH_3$ | $NHCH_3$ | 2,5-$(CH_3)_2$Ph |
| $CHF_2$ | $OCH_3$ | Ph |
| $CHF_2$ | $OCH_3$ | 2-$CH_3$Ph |
| $CHF_2$ | $OCH_3$ | 2,5-$(CH_3)_2$Ph |
| $CHF_2$ | $NHCH_3$ | Ph |
| $CHF_2$ | $NHCH_3$ | 2-$CH_3$Ph |
| $CHF_2$ | $NHCH_3$ | 2,5-$(CH_3)_2$Ph |
| $C_2H_5$ | $OCH_3$ | Ph |
| $C_2H_5$ | $OCH_3$ | 2-$CH_3$Ph |
| $C_2H_5$ | $OCH_3$ | 2,5-$(CH_3)_2$Ph |
| $C_2H_5$ | $NHCH_3$ | Ph |
| $C_2H_5$ | $NHCH_3$ | 2-$CH_3$Ph |
| $C_2H_5$ | $NHCH_3$ | 2,5-$(CH_3)_2$Ph |

The α-alkoxyphenylacetic acid compound represented by formula (1) may have isomers such as stereoisomers such as optical isomers based on an asymmetric carbon atoms and tautomers, and any isomer can be contained and used solely or in a mixture of any isomer ratio in the present invention.

The α-alkoxyphenylacetic acid compound represented by formula (1) may be in a form of a solvate (for example, hydrate) and it can be used in a form of a solvate in the present invention.

The α-alkoxyphenylacetic acid compound represented by formula (1) may be in a form of a crystal form and/or an amorphous form and it can be used in any form in the present invention.

The α-alkoxyphenylacetic acid compound represented by formula (1) is a compound described in WO95/27,693 pamphlet. These compounds can be synthesized, for example, by a method described in the pamphlet.

Next, the neonicotinoid represented by formula (2) for use in the composition for controlling pests according to the present invention along with α-alkoxyphenylacetic acid compound represented by formula (1) is described.

The neonicotinoid compound is a compound represented by formula (2)

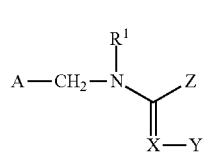

(2)

wherein A represents a 6-chloro-3-pyridyl group, a 2-chloro-5-thiazolyl group; a tetrahydrofuran-2-yl group or a tetrahydrofuran-3-yl group; Z represents a methyl group, an $NHR^2$ group, an $N(CH_3)R^2$ group or an $SR^2$ group; $R^1$ represents a hydrogen atom, a methyl group or an ethyl group; $R^2$ represents a hydrogen atom or a methyl group; or $R^1$ and $R^2$ together may form a $CH_2CH_2$ group or a $CH_2OCH_2$ group; X represents a nitrogen atom or a CH group; and Y represents a cyano group or a nitro group.

Specific examples of the neonicotinoid compound represented by formula (2) include:

a compound in which A is a 2-chloro-5-thiazolyl group, Z is an $NHCH_3$ group, $R^1$ is a hydrogen atom, X is a nitrogen atom, and Y is a nitro group (common name: clothianidin), a compound in which A is a 2-chloro-5-thiazolyl group, Z is an $N(CH_3)R^2$ group, $R^1$ and $R^2$ together form a $CH_2OCH_2$ group, X is a nitrogen atom, and Y is a nitro group (common name: thiamethoxam), a compound in which A is a 6-chloro-3-pyridyl group, Z is an $NHR^2$ group, $R^1$ and $R^2$ together form a $CH_2CH_2$ group, X is a nitrogen atom, and Y is a nitro group (common name: imidacloprid), a compound in which A is a 6-chloro-3-pyridyl group, Z is an $N(CH_3)R^2$ group, $R^1$ is an ethyl group, $R^2$ is a hydrogen atom, X is a CH group, and Y is a nitro group (common name: nitenpyram), a compound in which A is a tetrahydrofuran-3-yl group, Z is an $N(CH_3)R^2$ group, $R^1$ is a hydrogen atom, $R^2$ is a hydrogen atom, X is a nitrogen atom, and Y is a nitro group (common name: dinotefuran), a compound in which A is a 6-chloro-3-pyridyl group, Z is a methyl group, $R^1$ is a methyl group, X is a nitrogen atom, and Y is a cyano group (common name: acetamiprid), a compound in which A is a 6-chloro-3-pyridyl group, Z is an $SR^2$ group, $R^1$ and $R^2$ together form a $CH_2CH_2$ group, X is a nitrogen atom, and Y is a cyano group (common name: thiacloprid).

Of these, clothianidin, thiamethoxam and imidacloprid are preferable, and clothianidin is more preferable.

The neonicotinoid compound represented by formula (2) is a well-known compound, and described, for example, in "The Pesticide Manual", 14th edition, published by British Crop Protection Council, ISBN 1901396142, pp. 209, 598, 1,022. These compounds can be obtained from commercial agents or by preparation by well-known methods.

In the composition for controlling pests according to the present invention, the weight ratio of α-alkoxyphenylacetic acid compound represented by formula (1), for example, the compound (1a) or (1b) mentioned below to the neonicotinoid compound represented by formula (2), for example, either one of clothianidin, thiamethoxam and imidacloprid is typically in the range of 0.0125:1 to 500:1, preferably 0.025:1 to 100:1. In addition, when used as a dusting powder, the range of 0.025:1 to 40:1 is more preferable, and when used as a seed treatment agent, the range of 0.25:1 to 100:1 is more preferable.

The composition for controlling pests according to the present invention may be a simple mixture of an α-alkoxyphenylacetic acid compound represented by formula (1) and a neonicotinoid compound represented by formula (2) but typically an α-alkoxyphenylacetic acid compound represented by formula (1) and a neonicotinoid compound represented by formula (2) are mixed with an inert carrier along with a surfactant and other adjuvants as needed so that the mixture is formulated into an oil agent, an emulsion, a flowable agent, a wettable powder, a granulated wettable powder, a powder agent, a granule agent and so on. The composition for controlling pests mentioned above can be used as a seed treatment agent of the present invention as it is or added with other inert ingredients.

The total amount of the α-alkoxyphenylacetic acid compound represented by formula (1) and the neonicotinoid compound represented by formula (2) in the composition for controlling pests according to the present invention is typically in the range of 0.1 to 99% by weight, preferably 0.2 to 90% by weight.

Examples of the solid carrier used in formulation include fine powders or granules such as minerals such as kaolin clay, attapulgite clay, bentonite, montmorillonite, acid white clay, pyrophyllite, talc, diatomaceous earth and calcite; natural organic materials such as corn rachis powder and walnut husk powder; synthetic organic materials such as urea; salts such as calcium carbonate and ammonium sulfate; synthetic inorganic materials such as synthetic hydrated silicon oxide; and as a liquid carrier, aromatic hydrocarbons such as xylene, alkylbenzene and methylnaphthalene; alcohols such as 2-propanol, ethyleneglycol, propylene glycol, and ethylene glycol monoethyl ether; ketones such as acetone, cyclohexanone and isophorone; vegetable oil such as soybean oil and cotton seed oil; petroleum aliphatic hydrocarbons, esters, dimethylsulfoxide, acetonitrile and water.

Examples of the surfactant include anionic surfactants such as alkyl sulfate ester salts, alkylaryl sulfonate salts, dialkyl sulfosuccinate salts, polyoxyethylene alkylaryl ether phosphate ester salts, lignosulfonate salts and naphthalene sulfonate formaldehyde polycondensates; nonionic surfactants such as polyoxyethylene alkyl aryl ethers, polyoxyethylene alkylpolyoxypropylene block copolymers and sorbitan fatty acid esters and cationic surfactants such as alkyltrimethylammonium salts.

Examples of the other formulation auxiliary agents include water-soluble polymers such as polyvinyl alcohol and polyvinylpyrrolidone, polysaccharides such as Arabic gum, alginic acid and the salt thereof, CMC (carboxymethyl-cellulose), Xanthan gum, inorganic materials such as aluminum magnesium silicate and alumina sol, preservatives, coloring agents and stabilization agents such as PAP (acid phosphate isopropyl) and BHT.

The composition for controlling pests according to the present invention can protect a plant from damages by pests which eat or suck the following plants and cause other damages to the plants (for example, harmful Arthropod such as harmful insects and harmful acarids). Examples of the pests on which the composition for controlling pests according to the present invention has control effect include:

Hemiptera: planthoppers such as small brown planthopper (*Laodelphax striatellus*), brown rice planthopper (*Nilaparvata lugens*) and white-backed rice planthopper (*Sogatella furcifera*); leafhoppers such as green rice leafhopper (*Nephotettix cincticeps*) and green rice leafhopper (*Nephotettix virescens*); aphids such as cotton aphid (*Aphis gossypii*), green peach aphid (*Myzus persicae*), cabbage aphid (*Brevicoryne brassicae*), potato aphid (*Macrosiphum euphorbiae*), foxglove aphid (*Aulacorthum solani*), oat bird-cherry aphid (*Rhopalosiphum padi*) and tropical citrus aphid (*Toxoptera citricidus*); stink bugs such as green stink bug (*Nezara antennata*), bean bug (*Riptortus clavetus*), rice bug (*Leptocorisa chinensis*), white spotted spined bug (*Eysarcoris parvus*), brown marmorated stink bug (*Halyomorpha mista*) and tarnished plant bug (*Lygus lineolaris*); whiteflies such as greenhouse whitefly (*Trialeurodes vaporariorum*), sweetpotato whitefly (*Bemisia tabaci*) and silverleaf whitefly (*Bemisia argentifolii*); scales such as california red scale (*Aonidiella aurantii*), san Jose scale (*Comstockaspis perniciosa*), citrus snow scale (*Unaspis citri*), red wax scale (*Ceroplastes rubens*) and cottony cushion scale (*Icerya purchasi*); lace bugs; psyllids;

Lepidoptera: pyralid moths such as rice stem borer (*Chilo suppressalis*), yellow stem borer (*Tryporyza incertulas*), rice leafroller (*Cnaphalocrocis medinalis*), cotton leafroller (*Notarcha derogata*), indian meal moth (*Plodia interpunctella*), oriental corn borer (*Ostrinia furnacalis*), european corn borer (*Ostrinia nubilaris*), cabbage webworm (*Hellula undalis*) and bluegrass webworm (*Pediasia teterrellus*); owlet moths such as common cutworm (*Spodoptera litura*), beet armyworm (*Spodoptera exigua*), rice armyworm (*Pseudaletia separata*), cabbage armyworm (*Mamestra brassicae*), black cutworm (*Agrotis ipsilon*), beet semi-looper (*Plusia nigrisigna*), *Thoricoplusia* spp., *Heliothis* spp., and *Helicoverpa* spp.; Pieridae such as cabbage butterfly (*Pieris rapae*); tortricid moths such as *Adoxophyes* spp., oriental fruit moth (*Grapholita molesta*), soybean pod borer (*Leguminivora glycinivorella*), azuki bean podworm (*Matsumuraeses azukivora*), summer fruit tortrix (*Adoxophyes orana fasciata*), smaller tea tortrix (*Adoxophyes* sp.), oriental tea tortrix (*Homona magnanima*), apple tortrix (*Archips fuscocupreanus*), and codling moth (*Cydia pomonella*); leafblotch miners such as tea leaf roller (*Caloptilia theivora*), and apple leafminer (*Phyllonorycter ringoneella*); fruitworm moths such as peach fruit moth (*Carposina niponensis*); lyonetiid moths such as *Lyonetia* spp.; tussock moths such as *Lymantria* spp., and *Euproctis* spp.; yponomeutid moths such as diamondback moths (*Plutella xylostella*); gelechiid moths such as pink bollworm (*Pectinophora gossypiella*), and potato tubeworm (*Phthorimaea operculella*); tiger moths such as fall webworm (*Hyphantria cunea*); tineid moths such as casemaking clothes moth (*Tinea translucens*), and webbing clothes moth (*Tineola bisselliella*);

Thysanoptera: thrips such as yellow citrus thrip (*Frankliniella occidentalis*), melon thrip (*Thrips parmi*), yellow tea thrip (*Scirtothrips dorsalis*), onion thrip (*Thrips tabaci*), flower thrip (*Frankliniella intonsa*), tobacco thrip (*Frankliniella fusca*);

Diptera: leaf miners such as oriental house fly (*Musca domestica*), common house mosquito (Culex pipiens pallens), common horse fly (*Tabanus trigonus*), onion maggot (*Hylemya antiqua*), seedcorn maggot (*Hylemya platura*), hyrcanus group mosquito (*Anopheles sinensis*), rice leafminer (*Agromyza oryzae*), rice leafminer (*Hydrellia griseola*), rice stem maggot (*Chlorops oryzae*) and legume leafminer (*Liriomyza trifolii*); melon fly (*Dacus cucurbitae*), Mediterranean fruit fly (*Ceratitis capitata*);

Coleoptera: twenty-eight-spotted ladybird (*Epilachna vigintioctopunctata*), cucurbit leaf beetle (*Aulacophora femoralis*), striped flea beetle (*Phyllotreta striolata*), rice leaf beetle (*Oulema oryzae*), rice curculio (*Echinocnemus squameus*), rice water weevil (*Lissorhoptrus oryzophilus*), boll weevil (*Anthonomus grandis*), azuki bean weevil (*Callosobruchus chinensis*), hunting billbug (*Sphenophorus venatus*), Japanese beetle (*Popillia japonica*), cupreous chafer (*Anomala*

*cuprea*), corn root worms (*Diabrotica* spp.), Colorado beetle (*Leptinotarsa decemlineata*), click beetles (*Agriotes* spp.), cigarette beetle (*Lasioderma serricorne*), varied carper beetle (*Anthrenus verbasci*), red flour beetle (*Tribolium castaneum*), powder post beetle (*Lyctus brunneus*), white-spotted longicorn beetle (*Anoplophora malasiaca*), pine shoot beetle (*Tomicus piniperda*);

Orthoptera: Asiatic locust (*Locusta migratoria*), African mole cricket (*Gryllotalpa africana*), rice grasshopper (*Oxya yezoensis*), rice grasshopper (*Oxya japonica*);

Hymenoptera: Cabbage sawfly (*Athalia rosae*), leaf-cutting ant (*Acromyrmex* spp.), fire ant (*Solenopsis* spp.);

Blattaria: German cockroach (*Blattella germanica*), smokybrown cockroach (*Periplaneta fuliginosa*), american cockroach (*Periplaneta americana*), brown cockroach (*Periplaneta brunnea*) and oriental cockroach (*Blatta orientalis*);

Acarina: spider mites such as two-spotted spider mite (*Tetranychus urticae*), citrus red mite (*Panonychus citri*), and *Oligonychus* spp.; eriophyid mites such as pink citrus rust mite (*Aculops pelekassi*); tarosonemid mites such as broad mite (*Polyphagotarsonemus latus*); false spider mites; peacock mites; flour mites such as mould mite (*Tyrophagus putrescentiae*); house dust mites such as American house dust mite (*Dermatophagoides farinae*), European house dust mite (*Dermatophagoides ptrenyssnus*); cheyletid mites such as *Cheyletus eruditus, Cheyletus malaccensis, Cheyletus moorei*;

Nematodes: rice white-tip nematode (*Aphelenchoides besseyi*), strawberry bud nematode (*Nothotylenchus acris*).

Examples on which high control effects of the present invention are expected include aphids, thrips, leaf miners, horsehair worm, Colorado beetle, Japanese beetle, cupreous chafer, boll weevil, rice water weevil, tabacco thrip, corn root worms, diamondback moths, green caterpillar and soybean pod borer.

The composition for controlling pests according to the present invention is effective for pests such as the following plant diseases.

Diseases of rice: blast (*Magnaporthe grisea*), *Helminthosporium* leaf spot (*Cochliobolus miyabeanus*), sheath blight (*Rhizoctonia solani*), and bakanae disease (*Gibberella fujikuroi*).

Diseases of wheat: powdery mildew (*Erysiphe graminis*), Fusarium head blight (*Fusarium graminearum, F. avenacerum, F. culmorum, Microdochium nivale*), rust (*Puccinia striiformis, P. graminis, P. recondita*), pink snow mold (*Micronectriella nivale*), *Typhula* snow blight (*Typhula* sp.), loose smut (*Ustilago tritici*), bunt (*Tilletia caries*), eyespot (*Pseudocercosporella herpotrichoides*), leaf blotch (*Mycosphaerella graminicola*), glume blotch (*Stagonospora nodorum*), and yellow spot (*Pyrenophora tritici-repentis*).

Diseases of barley: powdery mildew (*Erysiphe graminis*), Fusarium head blight (*Fusarium graminearum, F. avenacerum, F. culmorum, Microdochium nivale*), rust (*Puccinia striiformis, P. graminis, P. hordei*), loose smut (*Ustilago nuda*), scald (*Rhynchosporium secalis*), net blotch (*Pyrenophora teres*), spot blotch (*Cochliobolus sativus*), leaf stripe (*Pyrenophora graminea*), and *Rhizoctonia* damping-off (*Rhizoctonia solani*).

Diseases of corn: smut (*Ustilago maydis*), brown spot (*Cochliobolus heterostrophus*), copper spot (*Gloeocercospora sorghi*), southern rust (*Puccinia polysora*), gray leaf spot (*Cercospora zeae-maydis*), and *Rhizoctonia* damping-off (*Rhizoctonia solani*).

Diseases of citrus: melanose (*Diaporthe citri*), scab (*Elsinoe fawcetti*), penicillium rot (*Penicillium digitatum, P. italicum*), and brown rot (*Phytophthora parasitica, Phytophthora citrophthora*).

Diseases of apple: blossom blight (*Monilinia mali*), canker (*Valla ceratosperma*), powdery mildew (*Podosphaera leucotricha*), *Alternaria* leaf spot (*Alternaria alternata* apple pathotype), scab (*Venturia inaequalis*), bitter rot (*Colletotrichum acutatum*), crown rot (*Phytophtora cactorum*), blotch (*Diplocarpon mali*), and ring rot (*Botryosphaeria berengeriana*).

Diseases of pear: scab (*Venturia nashicola, V. pirina*), black spot (*Alternaria alternata* Japanese pear pathotype), rust (*Gymnosporangium haraeanum*), and *phytophthora* fruit rot (*Phytophtora cactorum*);

Diseases of peach: brown rot (*Monilinia fructicola*), scab (*Cladosporium carpophilum*), and phomopsis rot (*Phomopsis* sp.).

Diseases of grape: anthracnose (*Elsinoe ampelina*), ripe rot (*Glomerella cingulata*), powdery mildew (*Uncinula necator*), rust (*Phakopsora ampelopsidis*), black rot (*Guignardia bidwellii*), and downy mildew (*Plasmopara viticola*).

Diseases of Japanese persimmon: anthracnose (*Gloeosporium kaki*), and leaf spot (*Cercospora kaki, Mycosphaerella nawae*).

Diseases of gourd: anthracnose (*Colletotrichum lagenarium*), powdery mildew (*Sphaerotheca fuliginea*), gummy stem blight (*Mycosphaerella melonis*), Fusarium wilt (*Fusarium oxysporum*), downy mildew (*Pseudoperonospora cubensis*), Phytophthora rot (*Phytophthora* sp.), and damping-off (*Pythium* sp.);

Diseases of tomato: early blight (*Alternaria solani*), leaf mold (*Cladosporium fulvum*), and late blight (*Phytophthora infestans*).

Diseases of eggplant: brown spot (*Phomopsis vexans*), and powdery mildew (*Erysiphe cichoracearum*).

Diseases of cruciferous vegetables: *Alternaria* leaf spot (*Alternaria japonica*), white spot (*Cercosporella brassicae*), clubroot (*Plasmodiophora brassicae*), and downy mildew (*Peronospora parasitica*).

Diseases of welsh onion: rust (*Puccinia allii*), and downy mildew (*Peronospora destructor*).

Diseases of soybean: purple seed stain (*Cercospora kikuchii*), sphaceloma scad (*Elsinoe glycines*), pod and stem blight (*Diaporthe phaseolorum* var. *sojae*), septoria brown spot (*Septoria glycines*), frogeye leaf spot (*Cercospora sojina*), rust (*Phakopsora pachyrhizi*), brown stem rot (*Phytophthora sojae*), and *Rhizoctonia* damping-off (*Rhizoctonia solani*).

Diseases of kidney bean: anthracnose (*Colletotrichum lindemthianum*).

Diseases of peanut: leaf spot (*Cercospora personata*), brown leaf spot (*Cercospora arachidicola*) and southern blight (*Sclerotium rolfsii*).

Diseases of garden pea: powdery mildew (*Erysiphe pisi*), and root rot (*Fusarium solani* f. sp. *pisi*).

Diseases of potato: early blight (*Alternaria solani*), late blight (*Phytophthora infestans*), pink rot (*Phytophthora erythroseptica*) and powdery scab (*Spongospora subterranean* f. sp. *subterranea*).

Diseases of strawberry: powdery mildew (*Sphaerotheca humuli*), and anthracnose (*Glomerella cingulata*).

Diseases of tea: net blister blight (*Exobasidium reticulatum*), white scab (*Elsinoe leucospila*), gray blight (*Pestalotiopsis* sp.), and anthracnose (*Colletotrichum theae-sinensis*).

Diseases of tobacco: brown spot (*Alternaria longipes*), powdery mildew (*Erysiphe cichoracearum*), anthracnose (*Colletotrichum tabacum*), downy mildew (*Peronospora tabacina*), and black shank (*Phytophthora nicotianae*).

Diseases of rapeseed: *sclerotinia* rot (*Sclerotinia sclerotiorum*), and *Rhizoctonia* damping-off (*Rhizoctonia solani*).

Diseases of cotton: *Rhizoctonia* damping-off (*Rhizoctonia solani*).

Diseases of sugar beet: *Cercospora* leaf spot (*Cercospora beticola*), leaf blight (*Thanatephorus cucumeris*), Root rot (*Thanatephorus cucumeris*), and *Aphanomyces* root rot (*Aphanomyces cochlioides*).

Diseases of rose: black spot (*Diplocarpon rosae*), powdery mildew (*Sphaerotheca pannosa*), and downy mildew (*Peronospora sparsa*).

Diseases of chrysanthemum and asteraceous plants: downy mildew (*Bremia lactucae*), leaf blight (*Septoria chrysanthemi-indici*), and white rust (*Puccinia horiana*).

Diseases of various groups: diseases caused by *Pythium* spp. (*Pythium aphanidermatum, Pythium debarianum, Pythium graminicola, Pythium irregulare, Pythium ultimum*), gray mold (*Botrytis cinerea*), and *Sclerotinia* rot (*Sclerotinia sclerotiorum*).

Disease of Japanese radish: *Alternaria* leaf spot (*Alternaria brassicicola*).

Diseases of turfgrass: dollar spot (*Sclerotinia homeocarpa*), and brown patch and large patch (*Rhizoctonia solani*).

Disease of banana: sigatoka (*Mycosphaerella fijiensis, Mycosphaerella musicola*).

Disease of sunflower: downy mildew (*Plasmopara halstedii*).

Seed diseases or diseases in the early stages of the growth of various plants caused by bacteria of *Aspergillus* genus, *Penicillium* genus, *Fusarium* genus, *Gibberella* genus, *Tricoderma* genus, *Thielaviopsis* genus, *Rhizopus* genus, *Mucor* genus, *Corticium* genus, *Phoma* genus, *Rhizoctonia* genus and *Diplodia* genus.

Viral diseases of various plants mediated by *Polymixa* genus or the *Olpidium* genus and so on.

In the case of spray treatment, a high control effect is expected in particular for plant diseases which occur in wheat, citrus, soy bean, kidney bean, cotton, rapeseed, grape, turfgrass, pear, peach, apple, peanut, tea, sugar beet, banana, rice or gourd among the above. Examples on which a particular high control effect is expected for plant diseases among the diseases which occur in these plants include pink snow mold (*Mycrodochium nivale*), *Rhizoctonia* damping-off (*Rhizoctonia solani*), *Fusarium* head blight (*Fusarium graminearum, F. avenacerum, F. culmorum, Microdochium nivale*), eyespot (*Pseudocercosporella herpotrichoides*) of wheat, diseases of citrus: melanose (*Diaporthe citri*), scab (*Elsinoe fawcetti*), purple seed stain (*Cercospora kikuchii*), rust (*Phakopsora pachyrhizi*) of soybean, *Rhizoctonia* damping-off (*Rhizoctonia solani*) of cotton, *Rhizoctonia* damping-off (*Rhizoctonia solani*), *sclerotinia* rot (*Sclerotinia sclerotiorum*) of rapeseed, anthracnose (*Elsinoe ampelina*), ripe rot (*Glomerella cingulata*), powdery mildew (*Uncinula necator*), black rot (*Guignardia bidwellii*), gray mold (*Botrytis cinerea*), dollar spot (*Sclerotinia homeocarpa*), brown patch (*Rhizoctonia solani*) of turfgrass, scab (*Venturia nashicola, V. pirina*) of pear, blossom blight (*Monilinia mali*), scab (*Venturia inaequalis*), powdery mildew (*Podosphaera leucotricha*), blotch (*Diplocarpon mali*), ring rot (*Botryosphaeria berengeriana*) of apple, brown rot (*Monilinia fructicola*), phomopsis rot (*Phomopsis* sp.) of peach, leaf spot (*Cercospora arachidicola*) of peanut, gray blight (*Pestalotiopsis* sp.), anthracnose (*Colletotrichum theae-sinensis*) of tea, *Cercospora* leaf spot (*Cercospora beticola*), leaf blight (*Thanatephorus cucumeris*), Root rot (*Thanatephorus cucumeris*) of sugar beat, sigatoka (*Mycosphaerella fijiensis, Mycosphaerella musicola*) of banana, blast (*Magnaporthe grisea*), bakanae disease (*Gibberella fujikuroi*) of rice, and *Rhizoctonia* damping-off (*Rhizoctonia solani*) of gourd family, gray mold (*Botrytis cinerea*), *Sclerotinia* rot (*Sclerotinia sclerotiorum*) of various groups.

In the case of seed treatment, a high control effect is expected particular for plant diseases which occur in corn, sorghum, rice, rapeseed, soy bean, potato, sugar beet, cotton among the above. Among plant diseases occurring in these plants, plant diseases on which particularly high effects are expected include *Rhizoctonia* damping-off, diseases caused by *Pythium* spp. and diseases caused by *Fusarium* spp.

Pests can be controlled by applying effective amounts of the α-alkoxyphenylacetic acid compound represented by formula (1) and the neonicotinoid compound represented by formula (2) to the pests or a place where the pests inhabit or a place (plant, soil) where the pests may inhabit.

Pests can be controlled by applying effective amounts of the α-alkoxyphenylacetic acid compound represented by formula (1) and the neonicotinoid compound represented by formula (2) to a plant or a place where a plant is allowed to grow. As a plant which is the object of application, stalk and leaves of the plant, seed of the plant, bulbs of the plant can be included. Here, the bulb means a bulb, corm, rhizoma, stem tuber, root tuber and rhizophore.

When the application is conducted to pests, a plant or the soil where the plant is allowed to grow, the α-alkoxyphenylacetic acid compound represented by formula (1) and the neonicotinoid compound represented by formula (2) may be separately applied for the same period, but they are typically applied as a composition for controlling pests of the present invention from the viewpoint of simplicity of the application.

The controlling method of the present invention includes treatment of stalk and leaves of a plant, treatment of the place where the plant is allowed to grow such as the soil, treatment of the seeds such as seed sterilization/seed coating and treatment of the bulb such as potato sets.

As the treatment of stalk and leaves of a plant in the control method of the present invention, specifically, for example, application onto the surface of the plant such as spraying to the stalk and leaves and spraying to the trunk can be included.

As the treatment of the soil in the control method of the present invention, for example, spraying onto the soil, admixing with the soil, perfusion of an agent liquid into the soil (irrigation of an agent liquid, injection into the soil, dripping of an agent liquid) can be included and the examples of the place to be treated include a planting hole, a furrow, peripheral of the planting hole, peripheral of the planting furrow, the entire surface of the growing area, the parts between the soil and the plant, area between roots, area beneath the trunk, main furrow, growing soil, box for raising seedlings, tray for raising seedlings, seedbed. The treatment can be performed before dissemination, at the time of dissemination, immediately after the dissemination, during the raising period of seedlings, before settled planting, at the time of settled planting and growing time after settled planting. In the soil treatment mentioned above, the active ingredients may be applied to the plant at the same time, or solid manure such as paste manure containing the active ingredients may be applied to the soil. The active ingredients may be mixed in irrigating liquid, and, for example, may be injected to irrigating facilities (irrigating tube, irrigating pipe, sprinkler, etc.), mixed into the flooding liquid between furrows, or mixed into a water culture medium. Alternatively, the irrigating liquid and the active ingredients may be mixed beforehand and, for example, used for treatment by an appropriate irrigating method including the irrigating method mentioned above and the other methods such as sprinkling and flooding.

Treatment of a seed in the control method of the present invention is, for example, a method for treating a seed, a bulb or the like to be protected from pests with a composition for controlling pests of the present invention and specific examples thereof include a spraying treatment in which a suspension of the composition for controlling pests of the present invention is atomized and sprayed on the seed surface or the bulb surface; smearing treatment in which a wettable powder, an emulsion, a flowable agent or the like of the composition for controlling pests of the present invention as it is or added with a small amount of water is applied on the seed surface or the bulb surface; immersing treatment in which the seed is immersed in a solution of the composition for controlling pests of the present invention for a certain period of time; film coating treatment and pellet coating treatment.

When a plant or the soil for growing a plant is treated with an α-alkoxyphenylacetic acid compound represented by formula (1) and a neonicotinoid compound represented by formula (2), the amount for the treatment may be changed depending on the kind of the plant to be treated, the kind and the occurring frequency of the pests to be controlled, formulation form, treatment period, climatic condition and so on but the total amount of the α-alkoxyphenylacetic acid compound represented by formula (1) and the neonicotinoid compound represented by formula (2) (hereinbelow referred to as the amount of the active ingredients) per 10,000 m$^2$ is typically 1 to 5000 g and preferably 2 to 200 g.

The emulsion, wettable powder, flowable agent or the like is typically diluted with water, and then sprinkled for treatment. In this case, the concentration of the active ingredients is typically in the range of 0.0001 to 3% by weight and preferably 0.0005 to 1% by weight. The powder agent, granule agent or the like is typically used for treatment without dilution.

In the treatment of seeds, the amount of the applied active ingredients is typically in the range of 0.001 to 20 g, preferably 0.01 to 5 g per 1 kg of seeds.

The control method of the present invention can be used in agricultural lands such as fields, paddy fields, lawns and orchards or in non-agricultural lands.

The present invention can be used to control diseases in agricultural lands for cultivating the following "plant" and the like without adversely affecting the plant and so on.

Examples of the crops are as follows:

crops: corn, rice, wheat, barley, rye, oat, sorghum, cotton, soybean, peanut, buckwheat, beet, rapeseed, sunflower, sugar cane, tobacco, etc.;

vegetables: solanaceous vegetables (eggplant, tomato, pimento, pepper, potato, etc.), cucurbitaceous vegetables (cucumber, pumpkin, zucchini, water melon, melon, squash, etc.), cruciferous vegetables (Japanese radish, white turnip, horseradish, kohlrabi, Chinese cabbage, cabbage, leaf mustard, broccoli, cauliflower, etc.), asteraceous vegetables (burdock, crown daisy, artichoke, lettuce, etc.), liliaceous vegetables (green onion, onion, garlic, and asparagus), ammiaceous vegetables (carrot, parsley, celery, parsnip, etc.), chenopodiaceous vegetables (spinach, Swiss chard, etc.), lamiaceous vegetables (*Perilla frutescens*, mint, basil, etc.), strawberry, sweet potato, *Dioscorea japonica*, colocasia, etc., flowers, foliage plants, turf grasses, fruits: pomaceous fruits (apple, pear, Japanese pear, Chinese quince, quince, etc.), stone fleshy fruits (peach, plum, nectarine, *Prunus mume*, cherry fruit, apricot, prune, etc.), citrus fruits (*Citrus unshiu*, orange, lemon, lime, grapefruit, etc.), nuts (chestnuts, walnuts, hazelnuts, almond, pistachio, cashew nuts, *macadamia* nuts, etc.), berries (blueberry, cranberry, blackberry, raspberry, etc.), grape, kaki fruit, olive, Japanese plum, banana, coffee, date palm, coconuts, etc., trees other than fruit trees; tea, mulberry, flowering plant, roadside trees (ash, birch, dogwood, Eucalyptus, *Ginkgo biloba*, lilac, maple, *Quercus*, poplar, Judas tree, *Liquidambar formosana*, plane tree, zelkova, Japanese arborvitae, fir wood, hemlock, juniper, *Pinus, Picea*, and *Taxus cuspidate*), etc.

The aforementioned "plants" include plants, to which resistance to HPPD inhibitors such as isoxaflutole, ALS inhibitors such as imazethapyr or thifensulfuron-methyl, EPSP synthetase inhibitors such as glyphosate, glutamine synthetase inhibitors such as the glufosinate, acetyl-CoA carboxylase inhibitors such as sethoxydim, PPO inhibitors such as flumioxazin, and herbicides such as bromoxynil, dicamba, 2,4-D, etc. has been conferred by a classical breeding method or genetic engineering technique.

Examples of a "plant" on which resistance has been conferred by a classical breeding method include rape, wheat, sunflower and rice resistant to imidazolinone ALS inhibitory herbicides such as imazethapyr, which are already commercially available under a product name of Clearfield (registered trademark). Similarly, there is soy bean on which resistance to sulfonylurea ALS inhibitory herbicides such as thifensulfuron-methyl has been conferred by a classical breeding method, which is already commercially available under a product name of STS soy bean. Similarly, examples on which resistance to acetyl-CoA carboxylase inhibitors such as trione oxime or aryloxy phenoxypropionic acid herbicides has been conferred by a classical breeding method include SR corn. The plant on which resistance to acetyl-CoA carboxylase inhibitors has been conferred is described in Proceedings of the National Academy of Sciences of the United States of America (Proc. Natl. Acad. Sci. USA), vol. 87, pp. 7175-7179 (1990). A variation of acetyl-CoA carboxylase resistant to an acetyl-CoA carboxylase inhibitor is reported in Weed Science, vol. 53, pp. 728-746 (2005) and a plant resistant to acetyl-CoA carboxylase inhibitors can be generated by introducing a gene of such an acetyl-CoA carboxylase variation into a plant by genetically engineering technology, or by introducing a variation conferring resistance into a plant acetyl-CoA carboxylase. Furthermore, plants resistant to acetyl-CoA carboxylase inhibitors or ALS inhibitors or the like can be generated by introducing a site-directed amino acid substitution variation into an acetyl-CoA carboxylase gene or the ALS gene of the plant by introduction a nucleic acid into which has been introduced a base substitution variation represented Chimeraplasty Technique (Gura T. 1999. Repairing the Genome's Spelling Mistakes. Science 285: 316-318) into a plant cell.

Examples of a plant on which resistance has been conferred by genetic engineering technology include corn, soy bean, cotton, rape, sugar beet resistant to glyphosate, which is already commercially available under a product name of RoundupReady (registered trademark), AgrisureGT, etc. Similarly, there are corn, soy bean, cotton and rape which are made resistant to glufosinate by genetic engineering technology, a kind, which is already commercially available under a product name of LibertyLink (registered trademark). A cotton made resistant to bromoxynil by genetic engineering technology is already commercially available under a product name of BXN likewise.

The aforementioned "plants" include genetically engineered crops produced using such genetic engineering techniques, which, for example, are able to synthesize selective toxins as known in genus *Bacillus*.

Examples of toxins expressed in such genetically engineered crops include: insecticidal proteins derived from *Bacillus cereus* or *Bacillus popilliae*; δ-endotoxins such as Cry1Ab, Cry1Ac, Cry1F, Cry1Fa2, Cry2Ab, Cry3A, Cry3Bb1 or Cry9C, derived from *Bacillus thuringiensis*; insecticidal proteins such as VIP1, VIP2, VIP3, or VIP3A; insecticidal proteins derived from nematodes; toxins generated by animals, such as scorpion toxin, spider toxin, bee toxin, or insect-specific neurotoxins; mold fungi toxins; plant lectin; agglutinin; protease inhibitors such as a trypsin inhibitor, a serine protease inhibitor, patatin, cystatin, or a papain inhibitor; ribosome-inactivating proteins (RIP) such as lycine, corn-RIP, abrin, luffin, saporin, or briodin; steroid-metabolizing enzymes such as 3-hydroxysteroid oxidase, ecdysteroid-UDP-glucosyl transferase, or cholesterol oxidase; an ecdysone inhibitor; HMG-COA reductase; ion channel inhibitors such as a sodium channel inhibitor or calcium channel inhibitor; juvenile hormone esterase; a diuretic hormone receptor; stilbene synthase; bibenzyl synthase; chitinase; and glucanase.

Moreover, toxins expressed in such genetically engineered crops also include: hybrid toxins of δ-endotoxin proteins such as Cry1Ab, Cry1Ac, Cry1F, Cry1Fa2, Cry2Ab, Cry3A, Cry3Bb1, Cry9C, Cry34Ab or Cry35Ab and insecticidal proteins such as VIP1, VIP2, VIP3 or VIP3A; partially deleted toxins; and modified toxins. Such hybrid toxins are produced from a new combination of the different domains of such proteins, using a genetic engineering technique. As a partially deleted toxin, Cry1Ab comprising a deletion of a portion of an amino acid sequence has been known. A modified toxin is produced by substitution of one or multiple amino acids of natural toxins.

Examples of such toxins and genetically engineered plants capable of synthesizing such toxins are described in EP-A-0 374 753, WO 93/07278, WO 95/34656, EP-A-0 427 529, EP-A-451 878, WO 03/052073, etc.

Toxins contained in such genetically engineered plants are able to confer resistance particularly to insect pests belonging to Coleoptera, Hemiptera, Diptera, Lepidoptera and Nematodes, to the plants.

Furthermore, genetically engineered plants, which comprise one or multiple insecticidal pest-resistant genes and which express one or multiple toxins, have already been known, and some of such genetically engineered plants have already been on the market. Examples of such genetically engineered plants include YieldGard (registered trademark) (a corn variety for expressing Cry1Ab toxin), YieldGard Rootworm (registered trademark) (a corn variety for expressing Cry3Bb1 toxin), YieldGard Plus (registered trademark) (a corn variety for expressing Cry1Ab and Cry3Bb1 toxins), Herculex I (registered trademark) (a corn variety for expressing phosphinotricine N-acetyl transferase (PAT) so as to confer resistance to Cry1Fa2 toxin and glufosinate), NuCOTN33B (registered trademark) (a cotton variety for expressing Cry1Ac toxin), Bollgard I (registered trademark) (a cotton variety for expressing Cry1Ac toxin), Bollgard II (registered trademark) (a cotton variety for expressing Cry1Ac and Cry2Ab toxins), VIPCOT (registered trademark) (a cotton variety for expressing VIP toxin), NewLeaf (registered trademark) (a potato variety for expressing Cry3A toxin), NatureGard (registered trademark) Agrisure (registered trademark) GT Advantage (GA21 glyphosate-resistant trait), Agrisure (registered trademark) CB Advantage (Bt11 corn borer (CB) trait), and Protecta (registered trademark).

The aforementioned "plants" also include crops produced using a genetic engineering technique, which have ability to generate antipathogenic substances having selective action.

A PR protein and the like have been known as such antipathogenic substances (PRPs, EP-A-0 392 225). Such antipathogenic substances and genetically engineered crops that generate them are described in EP-A-0 392 225, WO 95/33818, EP-A-0 353 191, etc.

Examples of such antipathogenic substances expressed in genetically engineered crops include: ion channel inhibitors such as a sodium channel inhibitor or a calcium channel inhibitor (KP1, KP4 and KP6 toxins, etc., which are produced by viruses, have been known); stilbene synthase; bibenzyl synthase; chitinase; glucanase; a PR protein; and antipathogenic substances generated by microorganisms, such as a peptide antibiotic, an antibiotic having a hetero ring, a protein factor associated with resistance to plant diseases (which is called a plant disease-resistant gene and is described in WO 03/000906). These antipathogenic substances and genetically engineered plants producing such substances are described in EP-A-0392225, WO95/33818, EP-A-0353191, etc.

The "plant" mentioned above includes plants on which advantageous characters such as characters improved in oil stuff ingredients or characters having reinforced amino acid content have been conferred by genetically engineering technology. Examples thereof include VISTIVE (registered trademark) (low linolenic soy bean having reduced linolenic content) or high-lysine (high-oil) corn (corn with increased lysine or oil content).

Furthermore, stack varieties are also included in which a plurality of advantageous characters such as the classic herbicide characters mentioned above or herbicide tolerance genes, insecticidal harmful insect resistance genes, antipathogenic substance producing genes, characters improved in oil stuff ingredients or characters having reinforced amino acid content are combined.

EXAMPLES

In the following, the present invention will be more specifically described by way of formulation examples, seed treatment formulation examples, and test examples. However, the present invention is not limited to the following examples. In the following examples, the part represents part by weight unless otherwise noted in particular.

The compound (1a) is an α-alkoxyphenylacetic acid compound represented by formula (1) wherein $X^1$ is a methyl group, $X^2$ is a methylamino group, and $X^3$ is a 2,5-dimethylphenyl group and the compound has an R type steric structure according to Cahn-Ingold-Prelog order rule, and represented by the following formula (1a).

(1a)

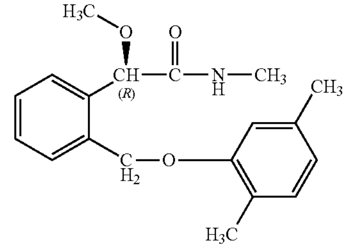

The compound (1b) is an α-alkoxyphenylacetic acid compound represented by formula (1) wherein X' is a methyl group, $X^2$ is a methylamino group, and $X^3$ is a 2,5-dimethylphenyl group and the compound is an racemic body and represented by the following formula (1b).

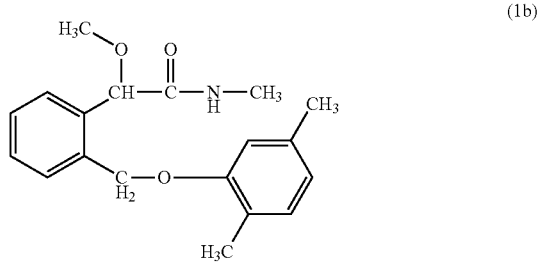 [SMILES: CNC(=O)C(OC)c1ccccc1COc1cc(C)ccc1C]

(1b)

Formulation Example 1

2.5 Parts of the compound (1a) or the compound (1b), 1.25 parts of clothianidin, 14 parts of polyoxyethylene styrylphenyl ether, 6 parts of calcium dodecyl benzene sulfonate and 76.25 parts of xylene are fully mixed, so as to obtain respective emulsions.

Formulation Example 2

Parts of the compound (1a) or the compound (1b), 5 parts of clothianidin, 35 parts of a mixture of white carbon and a polyoxyethylene alkyl ether sulfate ammonium salt (weight ratio 1:1) and 55 parts of water are mixed, and the mixture is subjected to fine grinding according to a wet grinding method, so as to obtain respective flowable agents.

Formulation Example 3

Parts of the compound (1a) or the compound (1b), 10 parts of imidacloprid, 1.5 parts of sorbitan trioleate and 28.5 parts of an aqueous solution containing 2 parts of polyvinyl alcohol are mixed, and the mixture is subjected to fine grinding according to a wet grinding method. Thereafter, 45 parts of an aqueous solution containing 0.05 part of Xanthan gum and 0.1 part of aluminum magnesium silicate is added to the resultant mixture, and 10 parts of propylene glycol is further added thereto. The obtained mixture is blended by stirring, so as to obtain respective flowables.

Formulation Example 4

Parts of the compound (1a) or the compound (1b), 20 parts of thiamethoxam, 1.5 parts of sorbitan trioleate and 28.5 parts of an aqueous solution containing 2 parts of polyvinyl alcohol are mixed, and the mixture is subjected to fine grinding according to a wet grinding method. Thereafter, 45 parts of an aqueous solution containing 0.05 part of Xanthan gum and 0.1 part of aluminum magnesium silicate is added to the resultant mixture, and 10 parts of propylene glycol is further added thereto. The obtained mixture is blended by stirring, so as to obtain respective flowable formulations.

Formulation Example 5

40 Parts of the compound (1a) or the compound (1b), 5 parts of imidacloprid, 5 parts of propylene glycol (manufactured by Nacalai Tesque), 5 parts of SoprophorFLK (manufactured by Rhodia Nikka), 0.2 parts of an anti-form C emulsion (manufactured by Dow Corning), 0.3 parts of proxel GXL (manufactured by Arch Chemicals) and 49.5 parts of ion-exchange water are mixed so as to obtain a bulk slurry. 150 parts of glass beads (diameter=1 mm) are put into 100 parts of the slurry, and the slurry is ground for 2 hours while being cooled with a cooling water. After ground, the resultant is filtered to remove the glass beads and respective flowables were obtained.

Formulation Example 6

50 Parts of the compound (1a) or the compound (1b), 0.5 part of thiamethoxam, 38.5 parts of NN kaolin clay (manufactured by Takehara Chemical Industrial), 10 parts of MorwetD425 and 1.5 parts of MorwerEFW (manufactured by Akzo Nobel Corp.) are mixed to obtain an AI premix. This premix was ground with a jet mill so as to obtain respective powders.

Formulation Example 7

1 Part of the compound (1a) or the compound (1b), 4 parts of clothianidin, 1 part of synthetic hydrated silicon oxide, 2 parts of calcium lignin sulfonate, 30 parts of bentonite and 62 parts of kaolin clay are fully ground and mixed, and the resultant mixture is added with water and fully kneaded, and then subjected to granulation and drying so as to obtain respective granules.

Formulation Example 8

1 Part of the compound (1a) or the compound (1b), 40 parts of thiamethoxam, 3 parts of calcium lignin sulfonate, 2 parts of sodium lauryl sulfate and 54 parts of synthetic hydrated silicon oxide are fully ground and mixed so as to obtain respective wettable powders.

Formulation Example 9

1 Part of the compound (1a) or the compound (1b), 2 parts of imidacloprid, 85 parts of kaolin clay and 10 parts of talc are fully ground and mixed so as to obtain respective powders.

Formulation Example 10

2 Parts of the compound (1a) or the compound (1b), 0.25 part of imidacloprid, 14 parts of polyoxyethylene styrylphenyl ether, 6 parts of calcium dodecyl benzene sulfonate and 77.75 parts of xylene are fully mixed, so as to obtain respective emulsions.

Formulation Example 11

10 Parts of the compound (1a) or the compound (1b), 2.5 parts of imidacloprid, 1.5 parts of sorbitan trioleate, 30 parts of an aqueous solution containing 2 parts of polyvinyl alcohol are subjected to fine grinding according to a wet grinding method. Thereafter, 47.5 parts of an aqueous solution containing 0.05 part of Xanthan gum and 0.1 part of aluminum magnesium silicate is added to the ground solution, and 10 parts of propylene glycol is further added thereto. The obtained mixture is blended by stirring, so as to obtain respective flowables.

Formulation Example 12

1 Part of the compound (1a) or the compound (1b), 20 parts of clothianidin, 1 part of synthetic hydrated silicon oxide, 2 parts of calcium lignin sulfonate, 30 parts of bentonite and 47 parts of kaolin clay are ground and mixed, and the resultant mixture is added with water and fully kneaded, and then subjected granulation and drying so as to obtain respective granules.

Formulation Example 13

40 Parts of the compound (1a) or the compound (1b), 1 part of thiamethoxam, 3 parts of calcium lignin sulfonate, 2 parts of sodium lauryl sulfate and 54 parts of synthetic hydrated silicon oxide are fully ground and mixed so as to obtain respective wettable powders.

Seed Treatment Example 1

An emulsion prepared as in Formulation example 1 is used for smear treatment in an amount of 500 ml per 100 kg of dried sorghum seeds using a rotary seed treatment machine (seed dresser, produced by Hans-Ulrich Hege GmbH) so as to obtain treated seeds.

Seed Treatment Example 2

A flowable prepared as in Formulation example 2 is used for smear treatment in an amount of 50 ml per 10 kg of dried rape seeds using a rotary seed treatment machine (seed dresser, produced by Hans-Ulrich Hege GmbH) so as to obtain treated seeds.

Seed Treatment Example 3

A flowable prepared as in Formulation example 3 is used for smear treatment in an amount of 40 ml per 10 kg of dried corn seeds using a rotary seed treatment machine (seed dresser, produced by Hans-Ulrich Hege GmbH) so as to obtain treated seeds.

Seed Treatment Example 4

Parts of a flowable agent prepared as in Formulation example 4, 5 parts of pigment BPD6135 (manufactured by Sun Chemical) and 35 parts of water are mixed to prepare a mixture. The mixture is used for smear treatment in an amount of 60 ml per 10 kg of dried rice seeds using a rotary seed treatment machine (seed dresser, produced by Hans-Ulrich Hege GmbH) so as to obtain treated seeds.

Seed Treatment Example 5

A powder agent prepared as in Formulation example 5 is used for powder coating treatment in an amount of 50 g per 10 kg of dried corn seeds so as to obtain treated seeds.

Seed Treatment Example 6

An emulsion prepared as in Formulation example 1 is used for smear treatment in an amount of 500 ml per 100 kg of dried sugar beet seeds using a rotary seed treatment machine (seed dresser, produced by Hans-Ulrich Hege GmbH) so as to obtain treated seeds.

Seed Treatment Example 7

A flowable prepared as in Formulation example 2 is used for smear treatment in an amount of 50 ml per 10 kg of dried soy bean seeds using a rotary seed treatment machine (seed dresser, produced by Hans-Ulrich Hege GmbH) so as to obtain treated seeds.

Seed Treatment Example 8

A flowable prepared as in Formulation example 3 is used for smear treatment in an amount of 50 ml per 10 kg of dried wheat seeds using a rotary seed treatment machine (seed dresser, produced by Hans-Ulrich Hege GmbH) so as to obtain treated seeds.

Seed Treatment Example 9

Parts of a flowable prepared as in Formulation example 4, 5 parts of pigment BPD6135 (manufactured by Sun Chemical) and 35 parts of water are mixed and the resultant mixture is used for smear treatment in an amount of 70 ml per 10 kg of potato tuber pieces using a rotary seed treatment machine (seed dresser, produced by Hans-Ulrich Hege GmbH) so as to obtain treated seeds.

Seed Treatment Example 10

A powder agent prepared as in Formulation example 5 is used for powder coating treatment in an amount of 40 g per 10 kg of dried cotton seeds so as to obtain treated seeds.

Test Example 1

A plastic pot was filled with sandy soil, and cucumber (variety: Sagamihanjiro) was then disseminated. The cucumber was allowed to grow in a green house for 12 days. A wettable powder of the compound (1b) and a wettable powder of clothianidin were respectively diluted with water and then tank-mixed so as to prepare tank-mixed liquids containing compound (1b) and clothianidin in predetermined concentration. The tank-mixed liquids were subjected to foliage application such that they could be sufficiently adhered to the leaves of the aforementioned cucumber plants. After completion of the foliage application, the plants were air-dried. Thereafter, a PDA nutrient medium containing spores of *Botrytis cinerea* was placed onto the leaf surface of the cucumber plants. They were placed at 12° C. under high humidity for 6 days after the inoculation, and thereafter control effect was checked.

As a comparison, the respective wettable powders described above were diluted with water in predetermined concentration so as to prepare a compound (1b) liquid and a clothianidin liquid respectively and they were subjected to similar disease control test.

Besides, the incidence of disease was also checked in the case of cucumber plants without the treatment with the agent in order to calculate the control value.

The following evaluation indexes were used at the time of the investigation. The incidence of disease was calculated by Equation 1 and the control value (%) was calculated by Equation 2 based on the incidence of disease.

As a result, a good effect was obtained.
Evaluation Index
  0: Diameter of maculation: 0 mm
  1: Diameter of maculation: 1-5 mm
  2: Diameter of maculation: 5-10 mm
  3: Diameter of maculation: 10-15 mm
  4: Diameter of maculation: 15-20 mm
  5: Diameter of maculation: >20 mm Incidence of disease=Σ(Evaluation index of leaves checked)×100/(Number of total leaves checked)    "Equation 1"

Control value=100(*A*−*B*)/*A*    "Equation 2"

A: Incidence of disease of plant in untreated area
B: Incidence of disease of plant in treated area Generally, the control value expected for the case where the given two kinds of active ingredient compounds are mixed and used for the treatment, the so-called control value expec tation is calculated from the following Colby's calculating equation.

$$E = X + Y - (X \times Y)/100 \quad \text{"Equation 3"}$$

X: Control value (%) when active ingredient compound A is used for treatment in M ppm Y: Control value (%) when active ingredient compound B is used for treatment in N ppm E: Control value (%) expected for the case where active ingredient compound A in M ppm and active ingredient compound B in N ppm are mixed and used for treatment (control value expectation)

"Synergetic effect"=(Actual control value)×100/(Control value expectation)

TABLE 2

| Compound (1b) | Clothianidin | Diameter of maculation | Control value |
|---|---|---|---|
| 12.5 ppm | 100 ppm | 9.0 mm | 67.7% |

Test Example 2

Soy bean is plated in a polyethylene cup and allowed to grow till the first true leaf stage and about 20 individuals of *Aulacorthum solani* Kaltenbach are allowed to parasitize the leaf. A wettable powder of the compound (1a) or compound (1b) and a wettable powder of clothianidin are respectively diluted with water and then tank-mixed so as to prepare tank-mixed liquids containing compound (1a) and clothianidin or compound (1b) and clothianidin in predetermined concentration. One day later, the mix solution mentioned above is sprayed on the soy bean in the ratio of 20 ml/cup. The number of *Aulacorthum solani* Kaltenbach is checked on the sixth day after the spraying and the control value is determined by the following equation.

Control value (%)={1−($Cb \times Tai$)/($Cai \times Tb$)}×100

Here, the characters in the expression represent the following meanings.

Cb: Number of the bugs before the treatment in the untreated area

Cai: Number of the bugs at the time of observation in the untreated area

Tb: Number of the bugs before the treatment in the treated area

Tai: Number of the bugs at the time of observation in the treated area

In the treated area, larger control effect is obtained in comparison with the untreated area.

Test Example 3

Corn seeds treated with the agent are prepared as in Seed treatment example 5, and they are sowed in a polyethylene cup and allowed to grow till the third leaf stage and about 20 individuals of *Rhopalosiphum padi* are allowed to parasitize the plant. The number of *Rhopalosiphum padi* is checked on the sixth day after they are left on the leaf and control value is determined by the following equation.

Control value (%)={1−($Cb \times Tai$)/($Cai \times Tb$)}×100

Here, the characters in the equation represent the following meanings.

Cb: Number of the bugs before the treatment in the untreated area

Cai: Number of the bugs at the time of observation in the untreated area

Tb: Number of the bugs before the treatment in the treated area

Tai: Number of the bugs at the time of observation in the treated area

In the treated area, larger control effect is obtained in comparison with the untreated area.

Test Example 4

An acetone solution of the compound (1b) and an acetone solution of clothianidin were mixed so as to prepare mixed liquids containing compound (1b) and clothianidin in predetermined concentration. These mixed liquids were allowed to adhere to the surface of seeds of cucumber plants (variety: Sagamihanjiro) so as to obtain treated seeds. The treated seeds were left untouched overnight and then disseminated on the soil which filled a plastic pot and covered with the soil, which had been mixed with a bran medium on which *Rhizoctonia solani* had been allowed to grow. They were allowed to grow in a greenhouse while irrigated and the number of non-budding seeds was checked on the seventh day after the dissemination and the incidence of disease was calculated by Equation 4. The control value was calculated by Equation 2 based on the incidence of disease. The incidence of disease was also checked in the case of seeds without the treatment with the agent in order to calculate the control value.

In addition, seeds treated with either an acetone solution of the compound (1b) or clothianidin in the predetermined concentration for comparison were obtained and similar tests were performed using these seeds.

The results are shown in Table 3.

Incidence of disease=(Number of no budding seeds)× 100/(Number of total disseminated seeds)     "Equation 4"

TABLE 3

| Compound (1b) | Clothianidin | Actual control value | Control value expectation | Synergistic effect |
|---|---|---|---|---|
| 10 g/Seed 100 kg | 200 g/Seed 100 kg | 70% | 39% | 179% |
| 0 g/Seed 100 kg | 200 g/Seed 100 kg | 4% | — | — |
| 10 g/Seed 100 kg | 0 g/Seed 100 kg | 35% | — | — |

INDUSTRIAL APPLICABILITY

According to the present invention, a composition for controlling pests having high activity and a method for effectively controlling pests can be provided.

The invention claimed is:

1. A composition for controlling pests comprising, as active ingredients, an α-alkoxyphenylacetic acid compound represented by formula (1):

(1)

wherein $X^1$ represents a methyl group; $X^2$ represents a methylamino group; and $X^3$ represents a 2,5-dimethylphenyl group;

and a Neonicotinoid compound represented by formula (2)

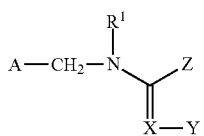

(2)

wherein A represents a 6-chloro-3-pyridyl group, a 2-chloro-5-thiazolyl group, a tetrahydrofuran-2-yl group or a tetrahydrofuran-3-yl group; Z represents a methyl group, an $NHR^2$ group, an $N(CH_3)R^2$ group or an $SR^2$ group, $R^1$ represents a hydrogen atom, a methyl group or an ethyl group; $R^2$ represents a hydrogen atom or a methyl group; or $R^1$ and $R^2$ together may form a $CH_2CH_2$ group or a $CH_2OCH_2$ group, X represents a nitrogen atom or a CH group; and Y represents a cyano group or a nitro group.

2. The composition for controlling pests according to claim 1, wherein the Neonicotinoid compound represented by formula (2) is selected from the group consisting of clothianidin, imidacloprid and thiamethoxam.

3. The composition for controlling pests according to claim 1 or 2, wherein a weight ratio of the α-alkoxyphenylacetic acid compound represented by formula (1) to the Neonicotinoid compound represented by formula (2) is in the range of 0.0125:1 to 500:1.

4. A method for controlling pests which comprises applying effective amounts of an α-alkoxyphenylacetic acid compound represented by formula (1):

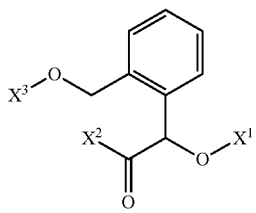

(1)

wherein $X^1$ represents a methyl group; $X^2$ represents a methylamino group; and $X^3$ represents a 2,5-dimethylphenyl group; and
a neonicotinoid compound represented by formula (2):

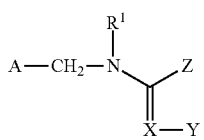

(2)

wherein A represents a 6-chloro-3-pyridyl group, a 2-chloro-5-thiazolyl group, a tetrahydrofuran-2-yl group or a tetrahydrofuran-3-yl group; Z represents a methyl group, an $NHR^2$ group, an $N(CH_3)R^2$ group or an $SR^2$ group, $R^1$ represents a hydrogen atom, a methyl group or an ethyl group; $R^2$ represents a hydrogen atom or a methyl group; or $R^1$ and $R^2$ together may form a $CH_2CH_2$ group or a $CH_2OCH_2$ group, X represents a nitrogen atom or a CH group; and Y represents a cyano group or a nitro group, to the pests or a locus where the pests inhabit.

5. A method for controlling pests which comprises applying effective amounts of an α-alkoxyphenylacetic acid compound represented by formula (1):

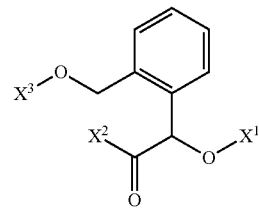

(1)

wherein $X^1$ represents a methyl group; $X^2$ represents a methylamino group; and $X^3$ represents a 2,5-dimethylphenyl group; and
a neonicotinoid compound represented by formula (2):

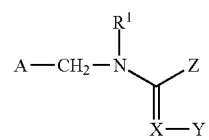

(2)

wherein A represents a 6-chloro-3-pyridyl group, a 2-chloro-5-thiazolyl group, a tetrahydrofuran-2-yl group or a tetrahydrofuran-3-yl group; Z represents a methyl group, an $NHR^2$ group, an $N(CH_3)R^2$ group or an $SR^2$ group, $R^1$ represents a hydrogen atom, a methyl group or an ethyl group; $R^2$ represents a hydrogen atom or a methyl group; or $R^1$ and $R^2$ together may form a $CH_2CH_2$ group or a $CH_2OCH_2$ group, X represents a nitrogen atom or a CH group; and Y represents a cyano group or a nitro group, to a plant or a locus where a plant is allowed to grow.

6. A seed treatment agent comprising an α-alkoxyphenylacetic acid compound represented by formula (1):

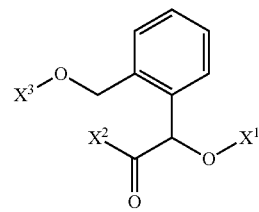

(1)

wherein $X^1$ represents a methyl group; $X^2$ represents a methylamino group; and $X^3$ represents a 2,5-dimethylphenyl group; and
a neonicotinoid compound represented by formula (2):

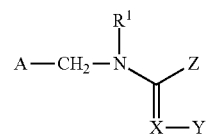

(2)

wherein A represents a 6-chloro-3-pyridyl group, a 2-chloro-5-thiazolyl group, a tetrahydrofuran-2-yl group or a tetrahydrofuran-3-yl group; Z represents a methyl group, an $NHR^2$ group, an $N(CH_3)R^2$ group or an $SR^2$ group, $R^1$ represents a hydrogen atom, a methyl group or an ethyl group; $R^2$ represents a hydrogen atom or a methyl group; or $R^1$ and $R^2$ together may form a $CH_2CH_2$ group or a $CH_2OCH_2$ group, X represents a nitrogen atom or a CH group; and Y represents a cyano group or a nitro group, as active ingredients.

7. A plant seed treated with effective amounts of an α-alkoxyphenylacetic acid compound represented by formula (1):

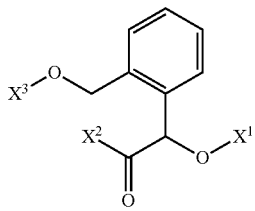

(1)

wherein $X^1$ represents a methyl group; $X^2$ represents a methylamino group; and $X^3$ represents a 2,5-dimethylphenyl group; and a neonicotinoid compound represented by formula (2):

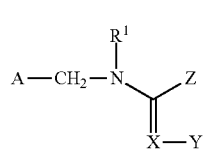

(2)

wherein A represents a 6-chloro-3-pyridyl group, a 2-chloro-5-thiazolyl group, a tetrahydrofuran-2-yl group or a tetrahydrofuran-3-yl group; Z represents a methyl group, an $NHR^2$ group, an $N(CH_3)R^2$ group or an $SR^2$ group, $R^1$ represents a hydrogen atom, a methyl group or an ethyl group; $R^2$ represents a hydrogen atom or a methyl group; or $R^1$ and $R^2$ together may form a $CH_2CH_2$ group or a $CH_2OCH_2$ group, X represents a nitrogen atom or a CH group; and Y represents a cyano group or a nitro group.

* * * * *